United States Patent
Sakaguchi (10) Patent No.: US 9,402,590 B2
(45) Date of Patent: Aug. 2, 2016

(54) THREE-DIMENSIONAL IMAGE PROCESSING APPARATUS AND X-RAY DIAGNOSTIC APPARATUS

(75) Inventor: Takuya Sakaguchi, Shioya-gun (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 897 days.

(21) Appl. No.: 12/578,862

(22) Filed: Oct. 14, 2009

(65) Prior Publication Data

US 2010/0092063 A1    Apr. 15, 2010

(30) Foreign Application Priority Data

Oct. 15, 2008    (JP) ................. 2008-266559

(51) Int. Cl.

| | | |
|---|---|---|
| *G06K 9/00* | (2006.01) | |
| *G06K 9/32* | (2006.01) | |
| *A61B 6/12* | (2006.01) | |
| *A61B 6/02* | (2006.01) | |
| *A61B 6/00* | (2006.01) | |
| *A61F 2/91* | (2013.01) | |

(52) U.S. Cl.

CPC . *A61B 6/12* (2013.01); *A61B 6/025* (2013.01); *A61B 6/4441* (2013.01); *A61B 6/541* (2013.01); *A61F 2/91* (2013.01); *A61F 2250/0098* (2013.01)

(58) Field of Classification Search

USPC .......................................... 382/154, 128, 293

See application file for complete search history.

(56) References Cited

U.S. PATENT DOCUMENTS

| | | | | |
|---|---|---|---|---|
| 5,581,671 A | * | 12/1996 | Goto ..................... | G06T 15/00 345/419 |
| 6,490,475 B1 | * | 12/2002 | Seeley ..................... | A61B 5/06 378/21 |
| 6,687,422 B1 | * | 2/2004 | Chen ..................... | G06T 3/4084 345/606 |
| 7,155,046 B2 | * | 12/2006 | Aben ..................... | G06T 7/0065 382/130 |
| 7,369,694 B2 | * | 5/2008 | Barfuss ..................... | A61B 6/12 382/131 |

(Continued)

FOREIGN PATENT DOCUMENTS

| | | |
|---|---|---|
| JP | 2004-230166 | 8/2004 |
| JP | 2005-288164 | 10/2005 |

OTHER PUBLICATIONS

Baxes, Digital Image Processing:Principles and Application, 1994 John Wiley and Sons, pp. 218-234.*

(Continued)

*Primary Examiner* — Kathleen Y Dulaney (74) *Attorney, Agent, or Firm* — Oblon, McClelland, Maier & Neustadt, L.L.P.

(57) ABSTRACT

Data of a plurality of projected images, which is photographed from different directions, regarding an object of interest is stored in an image data storage section. A feature point coordinates acquisition section acquires the three-dimensional coordinates regarding the axis of the object of interest on the basis of the feature information and photographing directions regarding the axis of the object of interest on at least two of the plurality of projected images stored in the image data storage section. A coordinates transformation section sets the three-dimensional coordinates system, which has the axis of the object of interest as one axis, on the basis of the three-dimensional coordinates information. A reconstruction processing section reconstructs three-dimensional image data based on the set three-dimensional coordinates system from the plurality of projected images stored in the image data storage section.

11 Claims, 11 Drawing Sheets

(56) References Cited

U.S. PATENT DOCUMENTS

| | | | | |
|---|---|---|---|---|
| 7,376,254 B2* | 5/2008 | Barth | ............... | G06K 9/00201 378/21 |
| 7,532,750 B2* | 5/2009 | Sasaki | ................ | G06T 11/008 345/427 |
| 7,869,663 B2* | 1/2011 | Buckland | ............... | A61B 3/102 382/131 |
| 8,009,936 B2* | 8/2011 | Oosawa | ............ | G06F 17/30259 382/128 |
| 8,131,031 B2* | 3/2012 | Lloyd | ................... | A61B 5/06 382/128 |
| 8,238,625 B2* | 8/2012 | Strommer | ............... | G06K 9/32 382/128 |
| 8,270,697 B2* | 9/2012 | Kim | ..................... | A61B 6/463 345/419 |
| 8,345,957 B2* | 1/2013 | Sakaguchi | ............. | A61B 6/032 382/154 |
| 8,712,129 B2* | 4/2014 | Strommer | ............... | G06K 9/32 382/128 |
| 2002/0090119 A1* | 7/2002 | Saito | .................. | G06F 19/3406 382/128 |
| 2002/0154801 A1* | 10/2002 | Ohishi | ................ | G06T 3/0087 382/132 |
| 2003/0088179 A1* | 5/2003 | Seeley | .................... | A61B 5/06 600/424 |
| 2003/0130576 A1* | 7/2003 | Seeley | .................... | A61B 5/06 600/426 |
| 2004/0160440 A1* | 8/2004 | Barth | ......................... | 345/419 |
| 2005/0220264 A1* | 10/2005 | Homegger | ............ | A61B 6/466 378/8 |
| 2005/0259882 A1* | 11/2005 | Dewaele | ................ | G06T 7/606 382/243 |
| 2006/0017748 A1* | 1/2006 | Ozawa | .................. | A61B 5/055 345/654 |
| 2006/0240378 A1* | 10/2006 | Weinstein | .............. | A61B 5/103 433/76 |
| 2007/0121778 A1* | 5/2007 | Shen | ..................... | G06T 7/0042 378/4 |
| 2007/0147671 A1* | 6/2007 | Di Vincenzo | ...... | H04N 13/0011 382/128 |
| 2007/0276224 A1* | 11/2007 | Lang | .................... | A61B 5/055 600/410 |
| 2008/0118115 A1* | 5/2008 | Williamson | ............ | G06T 15/00 382/128 |
| 2008/0137934 A1* | 6/2008 | Sakaguchi | ........... | A61B 6/4441 382/132 |
| 2008/0232554 A1* | 9/2008 | Heigl | ....................... | A61B 6/02 378/197 |
| 2008/0232664 A1* | 9/2008 | Nagamine | ........... | A61N 5/1048 382/131 |
| 2008/0287781 A1* | 11/2008 | Revie | ..................... | A61B 90/36 600/426 |
| 2009/0052613 A1* | 2/2009 | Sakaguchi | ........... | G01N 23/046 378/8 |
| 2009/0054910 A1* | 2/2009 | Zheng | ................ | A61B 17/1703 606/130 |
| 2009/0080737 A1* | 3/2009 | Battle | ................... | A61M 29/02 382/131 |
| 2009/0088830 A1* | 4/2009 | Mohamed | ................ | A61F 2/91 623/1.11 |
| 2009/0202118 A1* | 8/2009 | Holupka | ............... | G06T 3/0006 382/128 |
| 2010/0049036 A1* | 2/2010 | Kimh | .................. | A61B 6/5247 600/425 |
| 2010/0215228 A1* | 8/2010 | Shirahata | ............... | A61B 8/466 382/128 |
| 2010/0228340 A1* | 9/2010 | Erbel | ....................... | A61F 2/88 623/1.18 |

OTHER PUBLICATIONS

U.S. Appl. No. 12/756,553, filed Apr. 8, 2010, Ohishi.
Japanese Office Action mailed Aug. 20, 2013, in Japanese Patent Application No. 2009-237448 (with English Translation).

* cited by examiner

DISPLAYED WHILE ROTATING
IN AXIAL DIRECTION

THREE-DIMENSIONAL IMAGE PROCESSING APPARATUS AND X-RAY DIAGNOSTIC APPARATUS

CROSS-REFERENCE TO RELATED APPLICATIONS

This application is based upon and claims the benefit of priority from prior Japanese Patent Application No. 2008-266559, filed Oct. 15, 2008, the entire contents of which are incorporated herein by reference.

BACKGROUND OF THE INVENTION

1. Field of the Invention

The present invention relates to a three-dimensional image processing apparatus and an X-ray diagnostic apparatus which reconstruct a three-dimensional image from a plurality of X-ray images photographed from different directions.

2. Description of the Related Art

For example, JP-A-2005-288164 proposes a technique of reconstructing and displaying a local region, such as a stent, in a three-dimensional manner during the cardiovascular intervention. In such reconstruction processing, it is common that an image is generated in the table top coordinates system having a cephalocaudal axis, which has a head at the top and legs at the bottom, as a reference. When the image generated in this way is displayed on a monitor, for example, in a volume rendering format, the stent is displayed obliquely and rotates obliquely when it is made to rotate. In addition, when this image is displayed on the monitor, for example, in a slice format, the cross section of the stent is displayed in the elliptical shape. In this case, even if a doctor wants to check that there is no cracked place in the stent and the stent has sufficiently expanded, there is a problem that it is hard to check such matters through the displayed image. In addition, it takes time for a doctor to change the rotation axis manually during an intervention operation.

As described above, in the known display method, there are problems that an object of interest, such as a stent, is hard to observe and it takes time for a doctor to change the rotation axis manually during the intervention operation.

BRIEF SUMMARY OF THE INVENTION

In view of the above, it is an object of the present invention to provide a three-dimensional image processing apparatus and an X-ray diagnostic apparatus capable of providing an image in which an object of interest is easily observed.

According to an aspect of the present invention, there is provided a three-dimensional image processing apparatus including: a storage section that stores data of a plurality of projected images, which is photographed from different directions, regarding an object of interest; a coordinates acquisition section that acquires three-dimensional coordinates information regarding an axis of the object of interest on the basis of the feature information and photographing directions regarding the axis of the object of interest on at least two of the plurality of projected images; a coordinates transformation section that sets a three-dimensional coordinates system, which has the axis of the object of interest as one axis, on the basis of the three-dimensional coordinates information; and a reconstruction section that reconstructs three-dimensional image data based on the three-dimensional coordinates system from the plurality of projected images.

According to another aspect of the present invention, there is provided a three-dimensional image processing apparatus including: a storage section that stores data of a first three-dimensional image regarding an object of interest; a coordinates acquisition section that acquires three-dimensional coordinates information regarding an axis of the object of interest on the basis of the feature information regarding the axis of the object of interest on the first three-dimensional image; and a coordinates transformation section that sets a three-dimensional coordinates system, which has the axis of the object of interest as one axis, on the basis of the three-dimensional coordinates information.

According to another aspect of the present invention, there is provided an X-ray diagnostic apparatus including: an X-ray tube that generates an X-ray; an X-ray detector that detects an X-ray transmitted through a subject body on which medical equipment is placed; a rotation mechanism that makes the X-ray tube rotate around the subject body together with the X-ray detector; a storage section that stores data of a plurality of images photographed from different directions, the plurality of images being repeatedly photographed while the X-ray tube is rotating around the subject body together with the X-ray detector; a coordinates acquisition section that acquires three-dimensional coordinates information regarding an axis of the medical equipment on the basis of the feature information and photographing directions regarding the axis of the medical equipment on at least two of a plurality of projected images regarding the medical equipment; a coordinates transformation section that sets a three-dimensional coordinates system, which has the axis of the medical equipment as one axis, on the basis of the three-dimensional coordinates information; and a reconstruction section that reconstructs three-dimensional image data based on the three-dimensional coordinates system from the plurality of projected images.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Hereinafter, a three-dimensional image processing apparatus according to the present invention will be described with reference to the accompanying drawings. Moreover, in each embodiment, an explanation will be made assuming that a three-dimensional image processing apparatus is provided in an X-ray photographing apparatus.

First Embodiment

Figure 1:
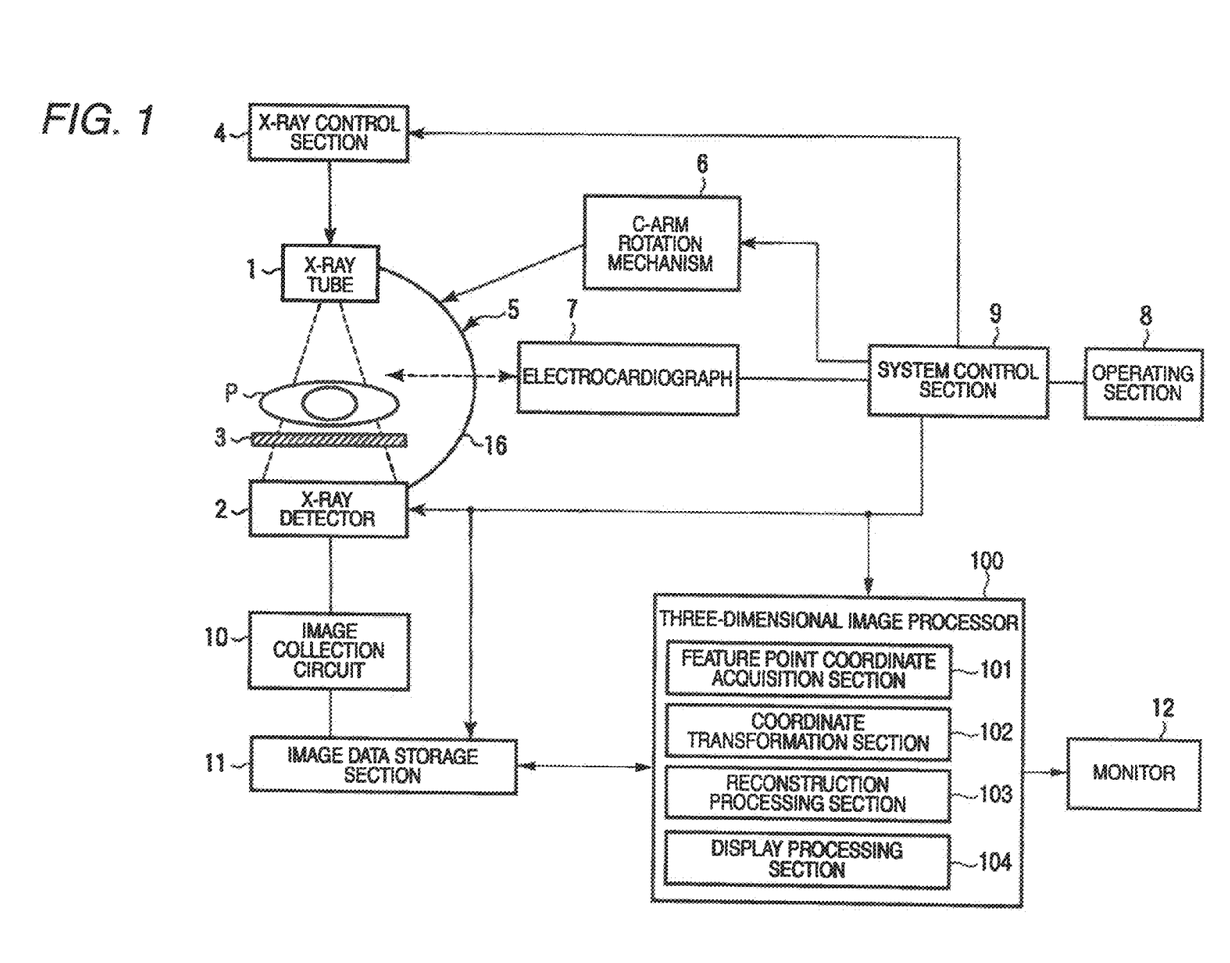
FIG. 1 is a view illustrating one embodiment of an X-ray photographing apparatus including a three-dimensional image processing apparatus according to a first embodiment of the present invention.

FIG. 1 is a block diagram illustrating an X-ray photographing apparatus including a three-dimensional image processing apparatus according to a first embodiment. The X-ray photographing apparatus has a C-arm device 5. The C-arm device 5 has a C arm 16, a floor or a ceiling support mechanism which supports the C arm 16 so as to be able to rotate around the three perpendicular axes, and a rotation driving source. An X-ray tube 1 is fixed to one end of the C arm 16. In order to generate an X-ray from the X-ray tube 1, an X-ray control section 4 applies a tube voltage between electrodes of the X-ray tube 1 and supplies a heating current to a negative-electrode filament of the X-ray tube 1 according to the control of a system control section 9. An X-ray detector 2 is fixed to the other end of the C arm 16. The X-ray tube 1 and the X-ray detector 2 face each other with a subject body P on a table top 3 interposed therebetween. The X-ray detector 2 is formed by a combination of an image intensifier and a TV camera, for example. Alternatively, the X-ray detector 2 is formed by a flat panel detector (FPD: flat X-ray detector) having semiconductor detecting elements arrayed in a matrix. In order to rotate the C arm 16, a C-arm rotation mechanism 6 supplies electric power to the driving source according to the control of the system control section 9. By repeatedly photographing while the C arm 16 is rotating, X-ray images (projected images) for a large quantity of directions required for three-dimensional image reconstruction can be acquired.

The rotation of the C arm 16, the application of a high voltage to the X-ray tube 1, and the reading of the signal of the X-ray detector 2 are controlled by the system control section 9, and the data of a plurality of projected images photographed from different directions is collected by an image collection circuit 10. In addition, in this X-ray photographing apparatus, an electrocardiograph 7 is provided to generate an electrocardiography by measuring the subject body P. An image data storage section 11 stores the data of the plurality of projected images, which is collected by the image collection circuit 10, so as to correspond with cardiac phase data which is acquired from the electrocardiography and the data of the photographing directions by the system control section 9. In addition, the cardiac phase is defined as an index for specifying each point of time within a period from the R wave of the electrocardiography to the next R wave and is usually expressed as a percent unit.

An operating section 8 is provided in order to transmit various commands from the user to the system control section 9 and has various input devices, such as a keyboard and a mouse. A monitor 12 is formed by a CRT (cathode-ray tube), a liquid crystal display (LCD), or the like.

Figure 2:
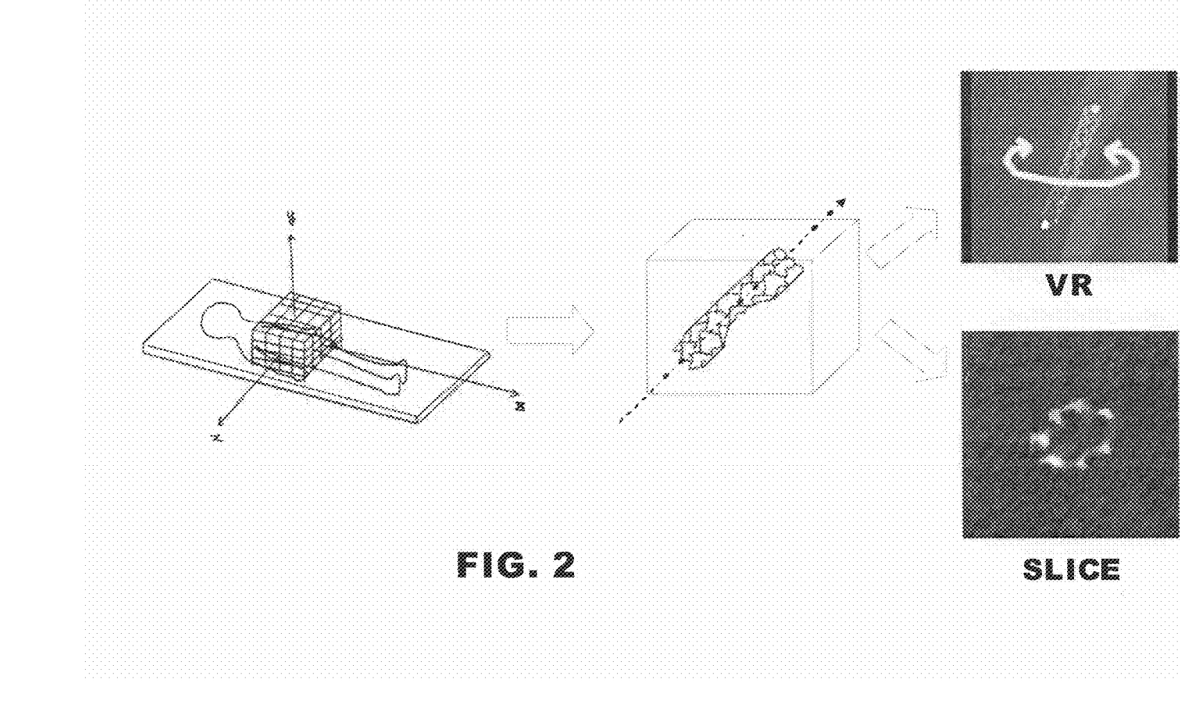
FIG. 2 is a view illustrating a stent displayed in the table top coordinates system.
Figure 3:
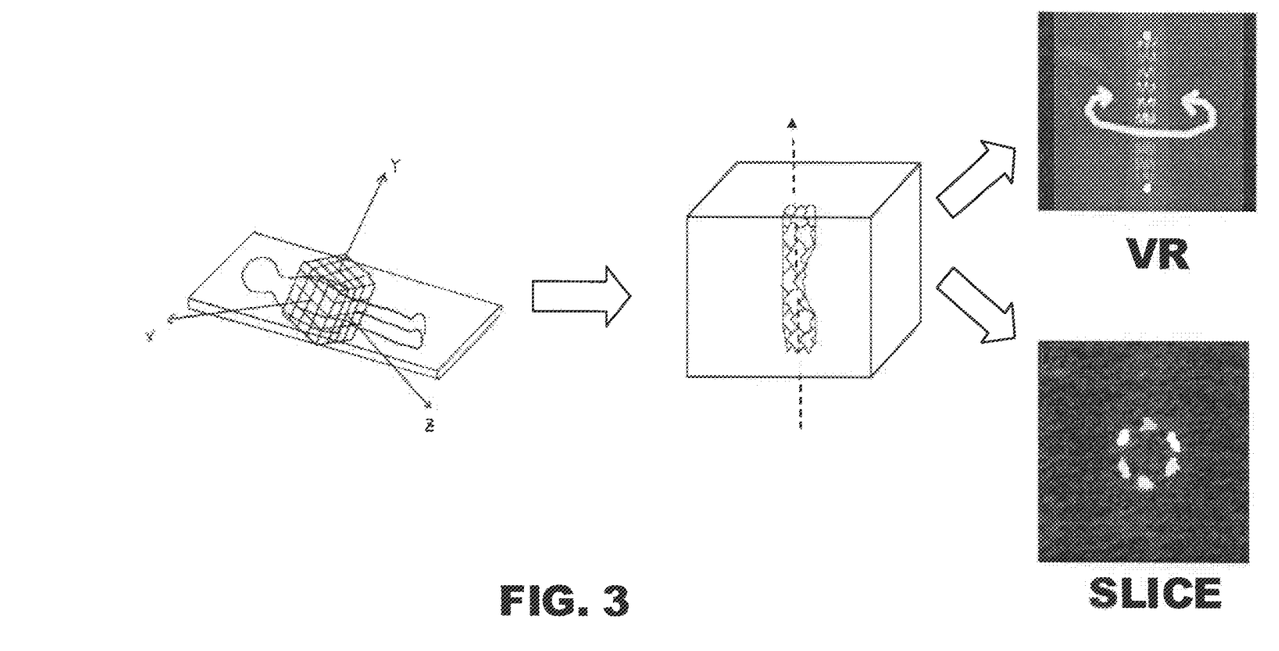
FIG. 3 is a view illustrating a stent displayed in the coordinates system having the stent as a reference.

A three-dimensional image processor 100 includes a feature point coordinates acquisition section 101, a coordinates transformation section 102, a reconstruction processing section 103, and a display processing section 104. As shown in FIG. 2, data (volume data) of a three-dimensional image is usually generated by reconstruction processing performed by defining the voxels in the coordinates system (table top coordinates system) having the table top 3 as a reference. When this volume data is displayed in a volume rendering format, a stent is displayed obliquely and rotates obliquely when it is made to rotate. In addition, when this volume data is displayed in a slice format, the cross section of the stent is displayed in the elliptical shape. Accordingly, in order to make the stent, which is an object of interest, easily observable, the three-dimensional image processor 100 reconstructs the volume data by defining the voxels in a direction along the central axis of the stent as shown in FIG. 3. In addition, although the stent is described as an object of interest in the present embodiment, a device inserted into the body, such as a balloon or an occlusion device, or a part of the inside of the body, such as a blood vessel, may also be used instead of the stent. In addition to the blood vessel of the heart, it is also useful when observing a device during paracentesis as an object of interest.

Figure 4:
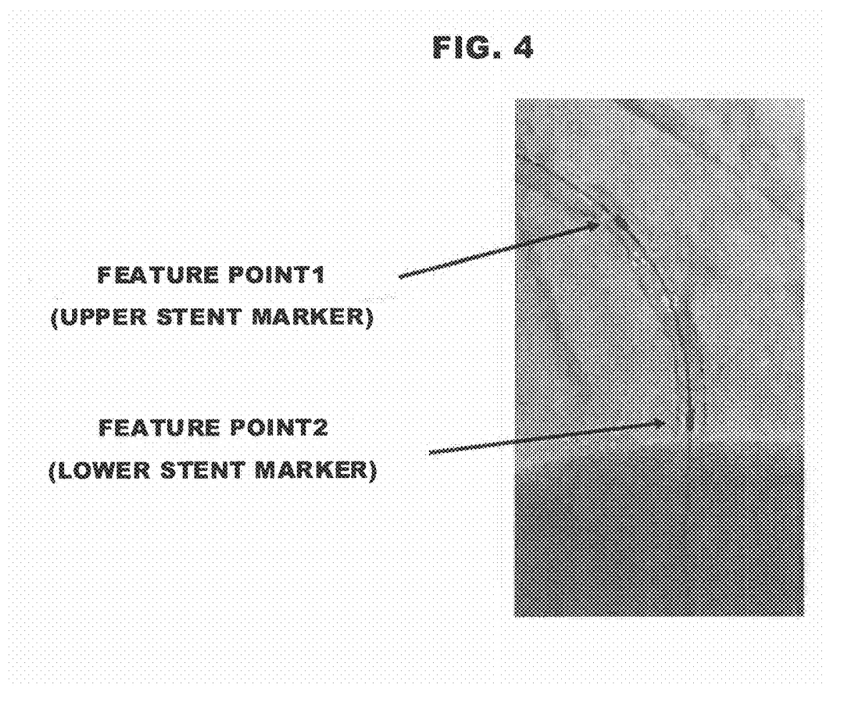
FIG. 4 is a view illustrating an example of an X-ray projected image of a stent.
Figure 5:
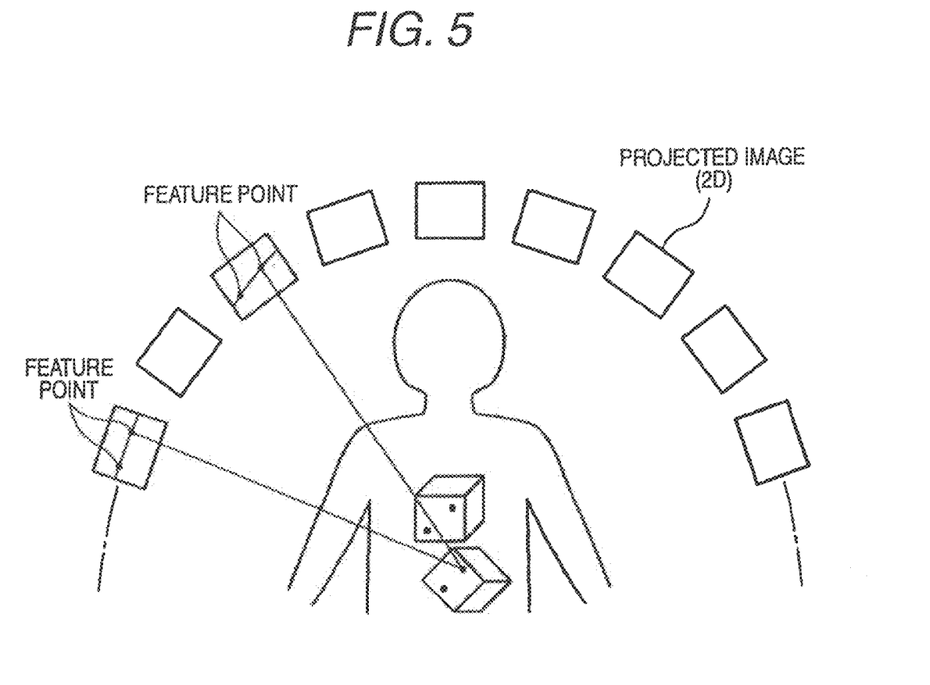
FIG. 5 is a view illustrating the processing for calculating the three-dimensional coordinates of the feature points.

The feature point coordinates acquisition section 101 acquires the three-dimensional coordinates (three-dimensional position) of the feature point by geometric calculation based on the two-dimensional coordinates of a plurality of feature points, which are designated on projected images of at least two frames with the same cardiac phase, and the photographing direction of each projected image. By matching the cardiac phase with the diastole, for example, blurring of an image caused by motion of the heart can be reduced. Here, two stent markers given to both ends of the central axis of the stent are used as the feature points. FIG. 4 is an example of a projected image obtained by photographing a stent. On the projected image, stent markers are displayed in a portion through which an X-ray is not transmitted. As shown in FIG. 5, data of projected images obtained by photographing the subject body from many directions is stored in the image data storage section 11. At timing when the projected images are photographed, it can be said that the stent exists at the same position in the three-dimensional space. Accordingly, the feature point coordinates acquisition section 101 can calculate the three-dimensional coordinates of the feature points on the basis of the two-dimensional coordinates of the feature points on the projected images of at least two frames and the photographing direction of each projected image.

The coordinates transformation section 102 sets the three-dimensional coordinates system having a straight line, which connects the three-dimensional coordinates of the two feature points, as one axis.

The reconstruction processing section 103 reconstructs the volume data by back-projection processing based on the plurality of projected images using the three-dimensional coordinates system set by the coordinates transformation section 102 as a reference. The volume data generated by reconstruction is stored in the image data storage section 11.

The display processing section 104 performs slice processing, maximum intensity projection (MIP) processing, or volume rendering (VR) processing on the volume data generated by the reconstruction processing section 103 and displays the slice image, the MIP image, or the VR image on the monitor 12.

Figure 6:
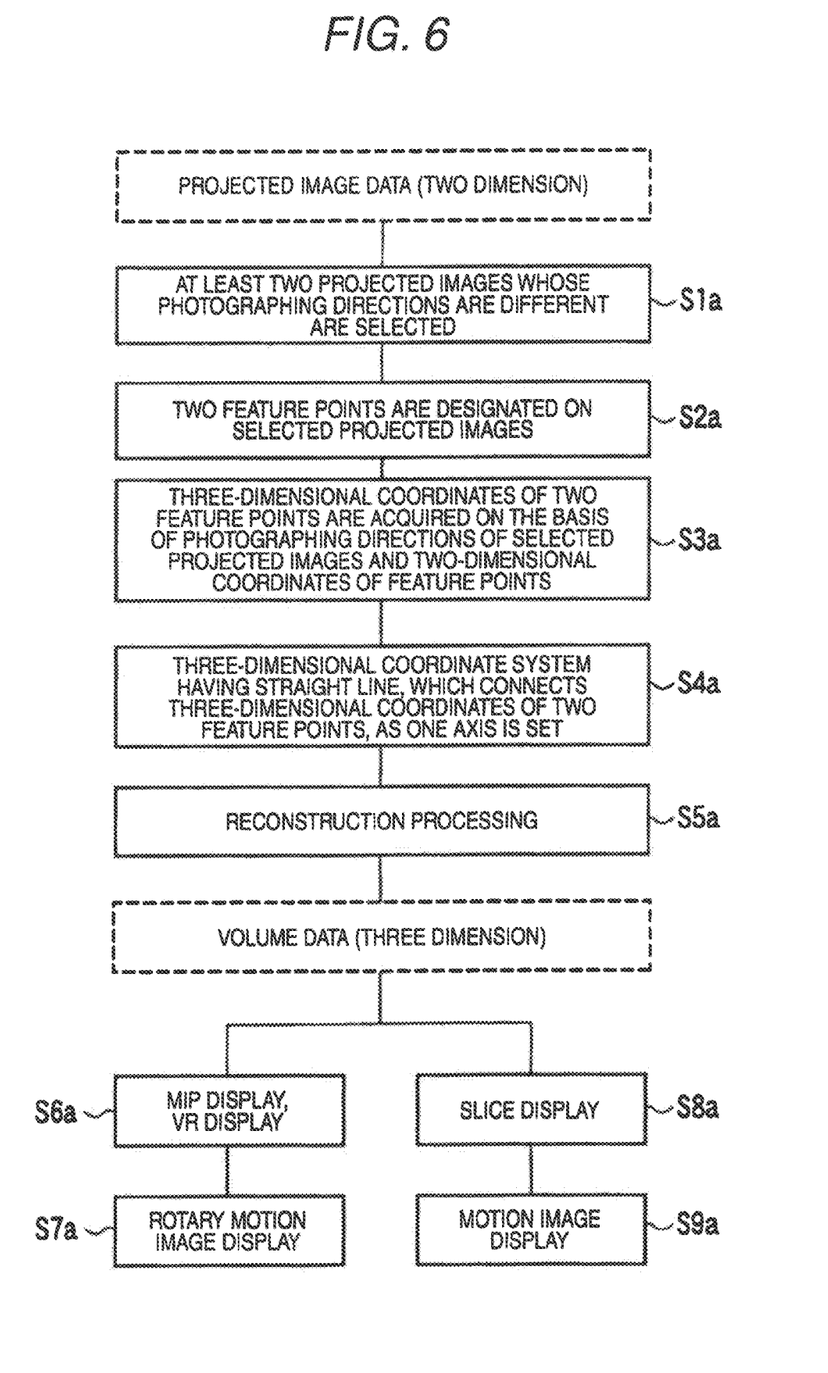
FIG. 6 is a flow chart illustrating an operation of a three-dimensional image processor in the first embodiment.

Next, an operation of the three-dimensional image processor 100 constructed in this way will be described. FIG. 6 is a flow chart illustrating the processing procedure of the three-dimensional image processor 100.

In FIG. 6, the three-dimensional image processor 100 selects at least two projected images photographed from different directions among the data of a plurality of projected images (step S1a). The three-dimensional image processor 100 receives the designation of the two feature points on the selected projected images (step S2a). For example, the operator designates stent markers as the feature points on the projected images. The feature point coordinates acquisition section 101 acquires the three-dimensional coordinates of the two feature points on the basis of the photographing directions of the selected projected images and the two-dimensional coordinates of the feature points (step S3a). The coordinates transformation section 102 sets the three-dimensional coordinates system having a straight line, which connects the three-dimensional coordinates of the two feature points, as one axis (step S4a).

The reconstruction processing section 103 reconstructs the volume data based on the set three-dimensional coordinates system, on the basis of the data of the plurality of projected images (step S5a). As a result, the volume data having the central axis of the stent as a reference is generated.

The display processing section 104 MIP-displays or VR-displays the volume data generated by the reconstruction processing section 103 on the monitor 12 (step S6a), and displays the MIP image or the VR image as a rotary motion image (step S7a). In addition, the display processing section 104 displays the generated volume data as slice images (sectional images) (step S8a), and displays a motion image by displaying the slices in a sequential manner (step S9a).

As described above, in the first embodiment, the three-dimensional coordinates of the two feature points are acquired, the three-dimensional coordinates system having as one axis the straight line which connects the three-dimensional coordinates of the two feature points is set, and the volume data based on the three-dimensional coordinates system is reconstructed from the plurality of projected images. In this way, the doctor can observe the volume rendering image, which rotates around the stent axis, during the operation and the cross section perpendicular to the stent axis is displayed on the slice image. Accordingly, since the stent section becomes circular, it becomes easy to measure the diameter through visual observation. As a result, an effect of shortening the operation time is obtained.

In addition, the display processing section 104 may draw a grid line in the grating shape when displaying a slice image. Since the displayed volume data exists along the axis which connects the two points, the diameter and radius of the stent can be approximately measured visually by observing the grid line on the sectional image.

Second Embodiment

In a second embodiment, a method of generating the second volume data along the direction of the central axis of a stent by reslicing based on the first volume data reconstructed in the table top coordinates system will be described.

Figure 7:
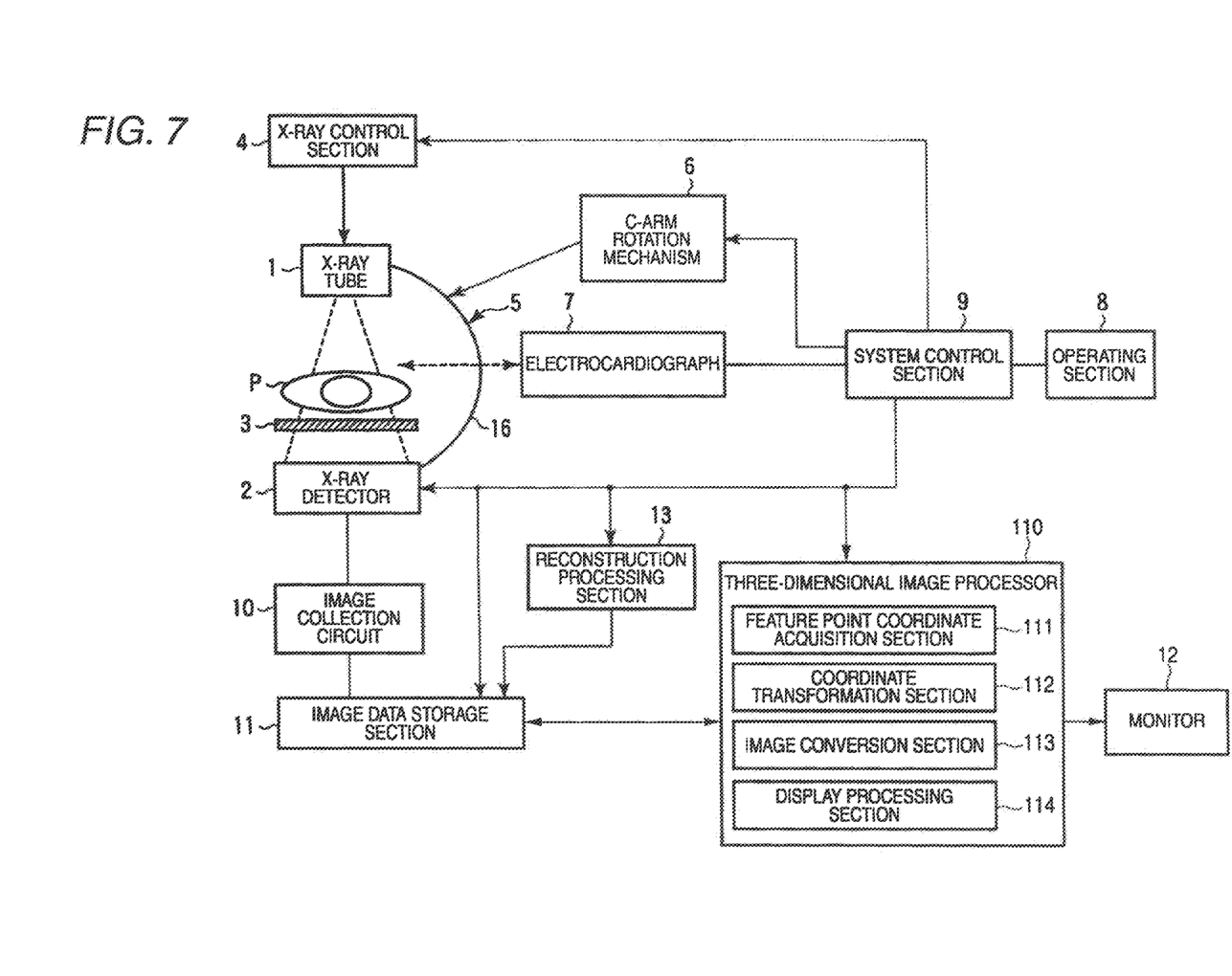
FIG. 7 is a view illustrating one embodiment of an X-ray photographing apparatus including a three-dimensional image processing apparatus according to a second embodiment of the present invention.

FIG. 7 is a block diagram illustrating an X-ray photographing apparatus including a three-dimensional image processing apparatus according to the second embodiment. In addition, the same components as in FIG. 1 are denoted by the same reference numerals, and a detailed explanation thereof will be omitted.

In FIG. 7, a reconstruction processing section 13 reconstructs the first volume data on the basis of a plurality of projected images which is photographed from different directions and is stored in the image data storage section 11. That is, the first volume data displayed in the table top coordinates system is assumed to be stored in the image data storage section 11 beforehand.

A three-dimensional image processing section 110 includes a feature point coordinates acquisition section 111, a coordinates transformation section 112, an image conversion section 113, and a display processing section 114.

The feature point coordinates acquisition section 111 acquires the three-dimensional coordinates of the feature points in the table top coordinates system in the first volume data stored in the image data storage section 11. The stent is a mesh-shaped long and narrow cylinder formed of a metal. The diameter is about 2 to 10 mm and the length is about 8 mm to 30 mm. Since metal absorbs X-rays, the stent is displayed white on the image. The image of the stent can be detected by recognizing the pattern of the shape by extracting pixels with brightness equal to or larger than the threshold value from the first volume data. For example, the two three-dimensional coordinates are acquired using markers at both ends of an image of the detected stent as the feature points.

The coordinates transformation section 112 sets the three-dimensional coordinates system having a straight line, which connects the two three-dimensional coordinates, as one axis.

The image conversion section 113 converts the first volume data into the second volume data by performing processing (reslice) involving slicing the first volume data again on the surface perpendicular to the one axis, in the three-dimensional coordinates system set by the coordinates transformation section 112.

The display processing section 114 performs slice processing, maximum intensity projection (MIP) processing, or volume rendering (VR) processing on the volume data converted by the image conversion section 113 and displays the slice image, the MIP image, or the VR image on the monitor 12.

Figure 8:
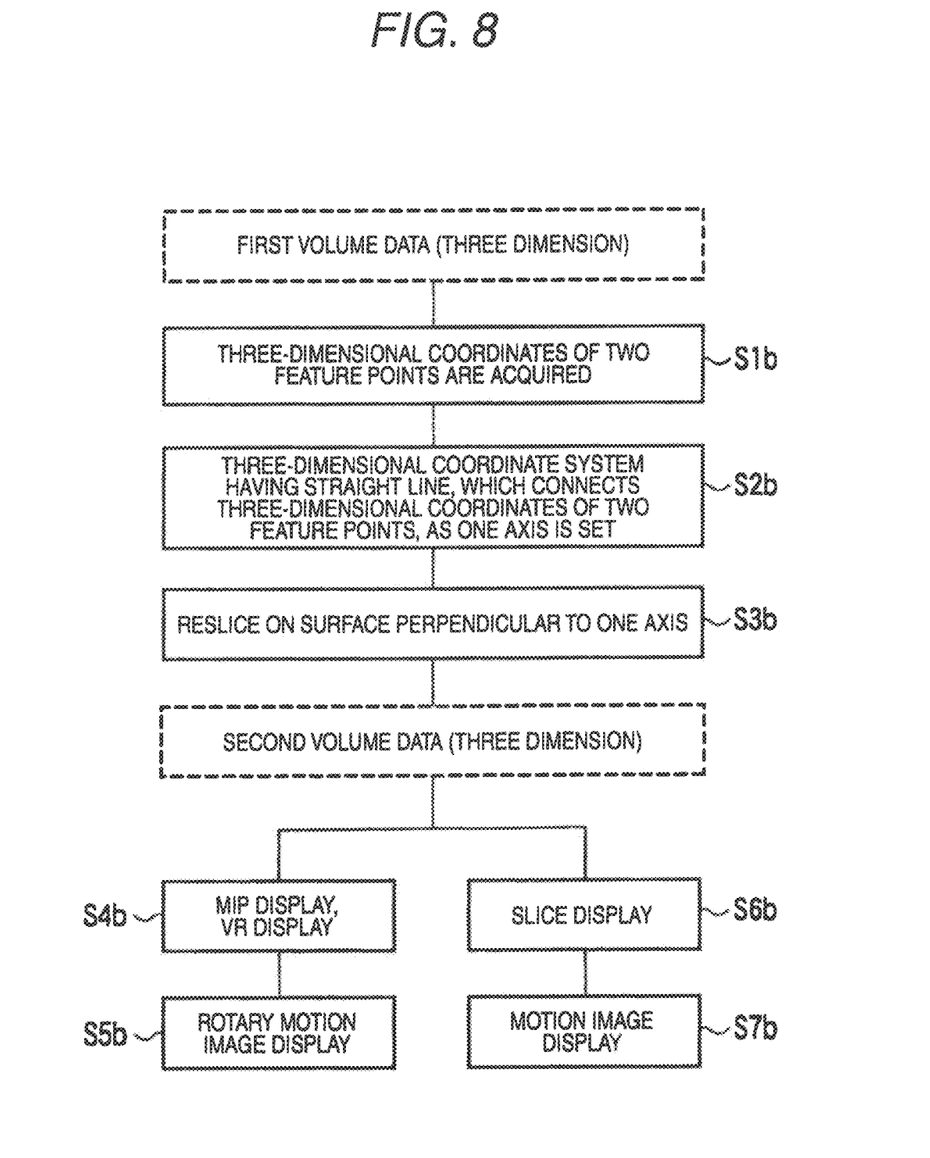
FIG. 8 is a flow chart illustrating the procedure of an operation of the three-dimensional image processor in the second embodiment.

Next, an operation of the three-dimensional image processor constructed in this way will be described. FIG. 8 is a flow chart illustrating the processing procedure of the three-dimensional image processor.

Figure 9:
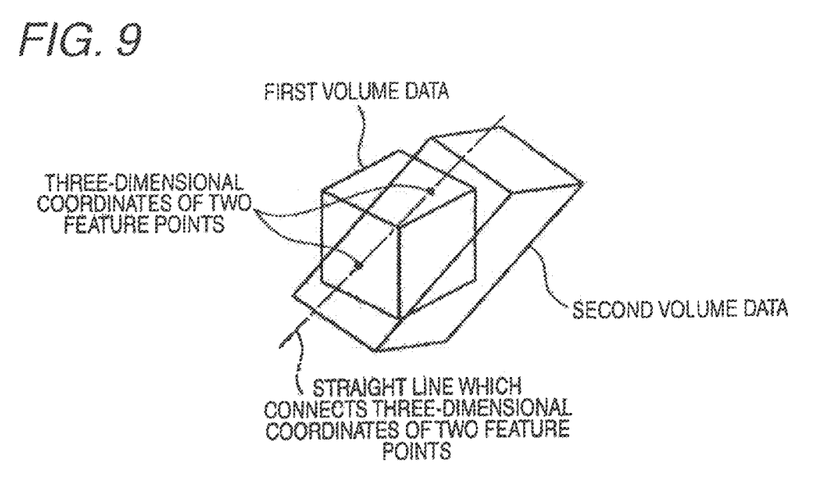
FIG. 9 is a view illustrating the processing for transformation from the first volume data to the second volume data.

The three-dimensional coordinates of the two feature points in the table top coordinates system in the first volume data stored in the image data storage section 11 are acquired (step S1b). The coordinates transformation section 112 sets the three-dimensional coordinates system having a straight line, which connects the acquired three-dimensional coordinates of the two feature points, as one axis (step S2b). The image conversion section 113 generates new volume data by reslicing the first volume data, which is stored in the image data storage section 11, on the surface perpendicular to the one axis in the set three-dimensional coordinates system, as shown in FIG. 9 (step S3b). In this reslice processing, for example, interpolation processing may be performed.

The display processing section 114 MIP-displays or VR-displays the volume data generated by the image conversion section 113 on the monitor 12 (step S4b), and displays the MIP image or the VR image as a rotary motion image (step S5b). In addition, the display processing section 104 displays the generated volume data as slice images (sectional images)

(step S6b), and displays a motion image by displaying the slices in a sequential manner (step S7b).

As described above, in the second embodiment, the three-dimensional coordinates system having a straight line, which connects the three-dimensional coordinates of the two feature points, as one axis is set and the first volume data displayed in the table top coordinates system is converted into the second volume data by reslicing the first volume data on the surface perpendicular to the one axis. In this manner, even when the volume data expressed in the table top coordinates system has already been generated, it is possible to obtain the volume data having the central axis of the stent as a reference. Accordingly, similarly to the first embodiment, it becomes possible to provide an image in which an object of interest, such as a stent, is easily observed.

Third Embodiment

In a third embodiment, display along the central axis direction of a stent is performed on the basis of the volume data reconstructed in the table top coordinates system.

An X-ray photographing apparatus including a three-dimensional image processing apparatus according to the third embodiment is configured to exclude the image conversion section 113 from the X-ray photographing apparatus shown in FIG. 7. Hereinafter, an explanation will be made with reference to FIG. 7.

Figure 10:
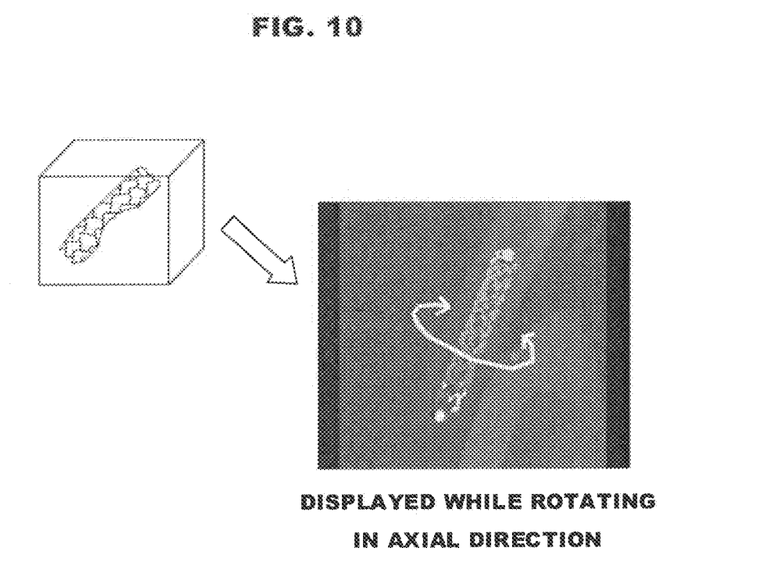
FIG. 10 is a view illustrating an example of the display using the three-dimensional image processing apparatus according to the third embodiment.

Although the reslice processing was performed in the image conversion section 113 in the second embodiment, there is a problem that this processing requires processing time. Therefore, in the third embodiment, the reslice processing of the image conversion section 113 is omitted and the display processing section 114 displays the volume data, which is reconstructed in the table top coordinates system, in a direction having a straight line connecting the two feature points as one axis in the three-dimensional coordinates system set by the coordinates transformation section 112. For example, the display processing section 114 VR-displays the volume data in the three-dimensional coordinates system set by the coordinates transformation section 112, and displays the volume data while rotating it in the one axis direction as shown in FIG. 10.

In this manner, in the third embodiment, the displayed stent is still inclined, but it becomes possible to perform rotational display in the central axis direction of the stent instead of the table top axis direction. The required information is the same as that in the second embodiment. In this way, an object of interest, such as a stent, can be easily observed by a simpler method than in the second embodiment.

In addition, the invention is not limited to the embodiments described above and may be embodied in practice by modifying the constituent components without departing from the scope and spirit of the invention. For example, specific modifications are as follows.

First Modification

In a first modification, the three-dimensional coordinates of the two feature points are acquired from the volume data in the second and third embodiments. In addition, this method may be applied to a very common three-dimensional image. Undoubtedly, it may be applied to a CT image, an MRI image, and the like.

Figure 11:
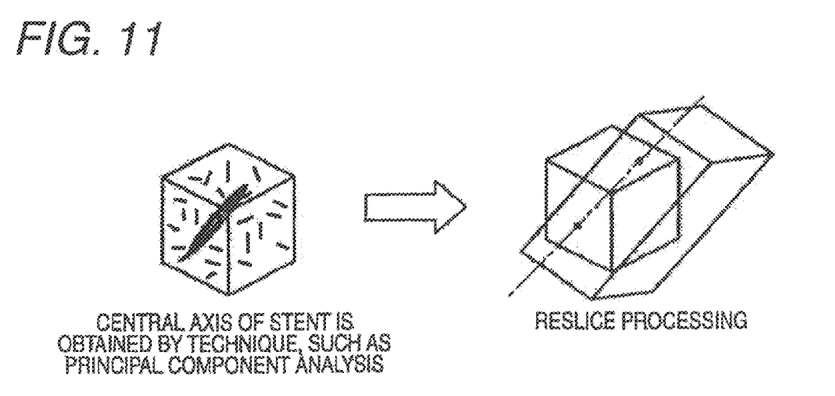
FIG. 11 is a view illustrating an operation in a first modification.

As shown in FIG. 11, in a three-dimensional image in which only the periphery of a stent is reconstructed, the stent which is an object of interest is reflected with the most intensity and the other portions with less intensity. Here, the direction vector and central axis of the stent are obtained from the three-dimensional image using a technique, such as principal component analysis. This may be realized by a common image processing method. The second volume data is obtained by performing the 'reslice' processing described in the second embodiment on the basis of the central axis obtained as a result. Moreover, in the third embodiment, VR display or the like may be performed in the direction of the obtained central axis.

Second Modification

In the above embodiments, the case where two feature points were acquired was described. In the case of a stent, there are mostly two markers at the upper and lower sides of the stent. Accordingly, the number of feature points is two. In a second modification, a case where there is one feature point will be described.

When there is one feature point, the method in each of the above embodiments may be applied by using the three-dimensional coordinates of the feature point and the information regarding the tangential line in contact with the feature point. For example, a stent with only one marker may be mentioned. In this case, since the number of feature points specified by the operator is one, the number of three-dimensional coordinates is also one. Therefore, the tangential line of the object (stent) existing at the three-dimensional coordinates of the feature point is calculated from the three-dimensional image by image processing, and each of the embodiments is performed by using the obtained tangential information.

In addition, when there are three or more feature points, if the feature points are approximately on a straight line, the method in each of the embodiments is applied using the straight line as an axis. When the three feature points are not on the straight line, normal display is performed without executing any processing.

Third Modification

In a third modification, when performing the reconstruction processing in the first embodiment, a straight line which connects the two feature points is used as an axis and the volume data for only a region around the axis is generated.

Figure 12:
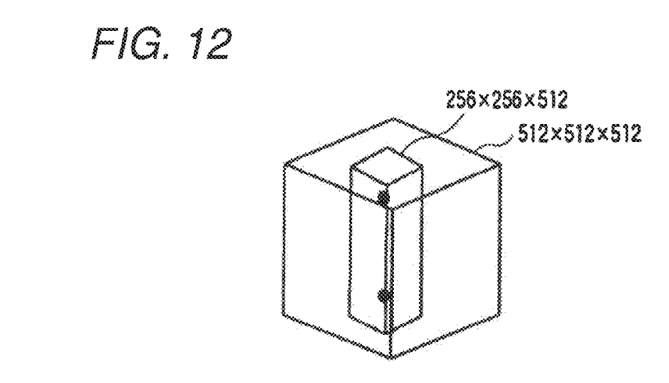
FIG. 12 is a view illustrating an operation in a third modification.

In the first embodiment, when creating the volume data in the coordinates system having as one axis the straight line which connects the two feature points, the stent exists as a long and narrow body near the axial center. Accordingly, the reconstruction processing section 103 generates the volume data with a rectangular parallelepiped shape having the one axis in the middle instead of a cubic shape. For example, as shown in FIG. 12, the volume data normally having 512×512×512 pixels is made to have 256×256×512 pixels. As a result, since the amount of volume data to be calculated is reduced, the computation time can be shortened.

Fourth Modification

In a fourth modification, when performing the reconstruction processing in the first embodiment, a straight line which connects the two feature points is used as an axis, and the volume data is generated such that the pixel pitch in the one axis direction is larger than that in a direction perpendicular to the one axis.

Figure 13:
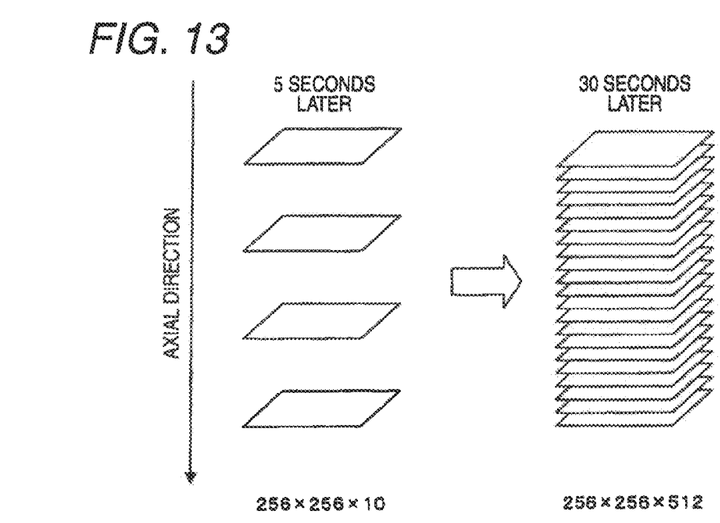
FIG. 13 is a view illustrating an operation in a fourth modification.

That is, the reconstruction processing section 103 makes the voxel pitch small in the stent surface direction (direction perpendicular to the one axis) and large in the one axis direction. As a result, since the amount of volume data to be calculated is reduced, the computation time is shortened. In addition, it may be made to become equal with time. For example, as shown in FIG. 13, the volume data with discrete 256×256×10 pixels is first created in the axial direction and then the volume data with 256×256×512 pixels is created by gradually narrowing the gap.

Fifth Modification

In a fifth modification, when performing the reconstruction processing in the first embodiment, a straight line which connects the two feature points is used as an axis and the three-dimensional image data is generated from the axis toward the outer periphery.

Figure 14:
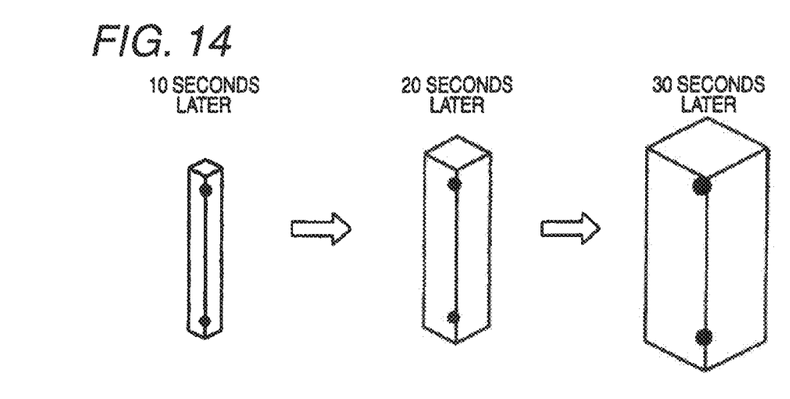
FIG. 14 is a view illustrating an operation in a fifth modification.

The reconstruction processing section 103 performs reconstruction based on the back-projection processing from the axial center set by the two feature points, and the display processing section 104 performs display sequentially from the generated portion. As a result, the user can observe a three-dimensional image in which an image near the axis is displayed first and which becomes large gradually, as shown in FIG. 14. In particular, since the stent exists as a long and narrow body near the axial center, the stent is displayed first and then the surrounding structure is displayed.

In addition, each of the functions in the present embodiments may be realized by installing a program, which is used to execute corresponding processing, in a computer, such as a workstation, and then loading the program into a memory. In this case, a program capable of causing a computer to execute a corresponding technique may be distributed in a state where the program is stored in a recording medium, such as a magnetic disk (for example, a floppy (registered trademark) disk or a hard disk), an optical disk (for example, a CD-ROM or a DVD), and a semiconductor memory.

Although the X-ray image for circulatory organs was used for explanation in the above embodiments, the embodiments are not limited to the X-ray image, and the range of the embodiments may be extended to medical images collected in other systems, such as a CT image, an MRI image, and an ultrasonic image.

Although the three-dimensional image processing apparatus was described as united with the X-ray photographing apparatus in the above embodiments, the three-dimensional image processing apparatus may be configured separately and independently as a three-dimensional image processing apparatus including an image data storage section, a three-dimensional image processor, and a monitor.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A three-dimensional image processing apparatus, comprising:
    a memory configured to store data of a plurality of projected images, which is photographed from different directions in a first three-dimensional coordinates system, regarding a stent inserted into a subject body;
    a coordinates acquisition circuit configured to acquire three-dimensional coordinates regarding two stent markers given to a central axis of the stent, based on two-dimensional coordinates of the two stent markers and photographing directions regarding two projected images of the plurality of projected images;
    a coordinates transformation circuit configured to set a second three-dimensional coordinates system having three orthogonal axes, wherein one axis of the three orthogonal axes is a straight line connecting the three-dimensional coordinates of the two stent markers, the second three-dimensional coordinates system being a three-dimensional orthogonal coordinates system that is translated and/or rotated with respect to the first three-dimensional coordinates system; and
    a reconstruction circuit configured to reconstruct three-dimensional image data by defining voxels in the second three-dimensional coordinates system from the plurality of projected images.

2. A three-dimensional image processing apparatus, comprising:
    a memory configured to store data of a plurality of projected images, which is photographed from different directions in a first three-dimensional coordinates system, regarding a stent inserted into a subject body;
    a coordinates acquisition circuit configured to acquire three-dimensional coordinates regarding two stent markers given to a central axis of the stent, based on two-dimensional coordinates of the two stent markers and photographing directions regarding two projected images of the plurality of projected images;
    a coordinates transformation circuit configured to set a second three-dimensional coordinates system having three orthogonal axes, wherein one axis of the three orthogonal axes is a straight line connecting the three-dimensional coordinates of the two stent markers; and
    a reconstruction circuit configured to reconstruct three-dimensional image data by defining voxels in the second three-dimensional coordinates system from the plurality of projected images.

3. The apparatus according to claim 2,
wherein the plurality of projected images are images regarding a portion which moves periodically over a plurality of periods, and
the coordinates acquisition circuit is configured to acquire the three-dimensional coordinates of the two stent markers from a plurality of images corresponding to approximately the same phase.

4. The apparatus according to claim 2,
wherein the reconstruction circuit is configured to generate the three-dimensional image data so as to be restricted to a region near the one axis.

5. The apparatus according to claim 2,
wherein the reconstruction circuit generates the three-dimensional image data such that a pixel pitch in a direction of the one axis is larger than that in a direction perpendicular to the one axis.

6. The apparatus according to claim 2,
wherein the reconstruction circuit generates the three-dimensional image data from the one axis toward an outer periphery.

7. An X-ray diagnostic apparatus, comprising:
    an X-ray tube configured to generate an X-ray;
    an X-ray detector configured to detect an X-ray transmitted through a subject body in which a stent is placed;
    a rotation frame configured to rotate the X-ray tube rotate around the subject body together with the X-ray detector;
    a memory configured to store data of a plurality of images photographed from different directions in a first three-dimensional coordinates system, the plurality of images being repeatedly photographed while the X-ray tube is rotating around the subject body together with the X-ray detector;

a coordinates acquisition circuit configured to acquire three-dimensional coordinates regarding two stent markers given to a central axis of the stent, based on two-dimensional coordinates of the two stent markers and photographing directions regarding two projected images of the plurality of projected images;

a coordinates transformation circuit configured to set a second three-dimensional coordinates system having three orthogonal axes, wherein one axis of the three orthogonal axes is a straight line connecting the three-dimensional coordinates of the two stent markers, the second three-dimensional coordinates system being a three-dimensional orthogonal coordinates system that is translated and/or rotated with respect to the first three-dimensional coordinates system; and a reconstruction circuit configured to reconstruct three-dimensional image data by defining voxels in the second three-dimensional coordinates system from the plurality of projected images.

8. An X-ray diagnostic apparatus, comprising:

an X-ray tube configured to generate an X-ray;

an X-ray detector configured to detect an X-ray transmitted through a subject body in which a stent is placed;

a rotation frame configured to rotate the X-ray tube rotate around the subject body together with the X-ray detector;

a memory configured to store data of a plurality of projected images, which is photographed from different directions in a first three-dimensional coordinates system, regarding a stent inserted into a subject body;

a coordinates acquisition circuit configured to acquire three-dimensional coordinates regarding two stent markers given to a central axis of the stent, based on two-dimensional coordinates of the two stent markers and photographing directions regarding two projected images of the plurality of projected images;

a coordinates transformation circuit configured to set a second three-dimensional coordinates system having three orthogonal axes, wherein one axis of the three orthogonal axes is a straight line connecting the three-dimensional coordinates of the two stent markers; and a reconstruction circuit configured to reconstruct three-dimensional image data by defining voxels in the second three-dimensional coordinates system from the plurality of projected images.

9. The apparatus according to claim 8, wherein the plurality of projected images are images regarding a portion which moves periodically over a plurality of periods, and the coordinates acquisition circuit is configured to acquire the three-dimensional coordinates of the two stent markers from a plurality of images corresponding to approximately the same phase.

10. The apparatus according to claim 8, wherein the reconstruction circuit is configured to generate the three-dimensional image data so as to be restricted to a region near the one axis.

11. The apparatus according to claim 8, wherein the reconstruction circuit generates the three-dimensional image data such that a pixel pitch in a direction of the one axis is larger than that in a direction perpendicular to the one axis.

* * * * *